United States Patent [19]

Hardcastle et al.

[11] Patent Number: 4,946,447
[45] Date of Patent: Aug. 7, 1990

[54] PROTECTIVE COVER FOR HYPODERMIC NEEDLE

[76] Inventors: Samuel L. Hardcastle, P.O. Box 325, Union, Mo. 63084; Yit K. Lee, 8528 Douglas Ct., Brentwood, Mo. 63144

[21] Appl. No.: 310,780
[22] Filed: Feb. 14, 1989
[51] Int. Cl.⁵ .............................................. A61M 5/32
[52] U.S. Cl. ..................................... 604/198; 604/263
[58] Field of Search ................ 604/198, 263, 187, 192

[56] References Cited

U.S. PATENT DOCUMENTS

| | | | |
|---|---|---|---|
| 2,571,653 | 10/1951 | Bastien | 128/215 |
| 3,563,239 | 2/1971 | Hill | 128/215 |
| 3,890,971 | 6/1975 | Leeson et al. | 128/215 |
| 4,356,822 | 11/1982 | Winstead-Hall | 128/215 |
| 4,373,526 | 2/1983 | Kling | 604/198 |
| 4,425,120 | 11/1984 | Sampson et al. | 604/198 |
| 4,643,722 | 2/1987 | Smith, Jr. | 604/192 |
| 4,655,751 | 4/1987 | Harbaugh | 604/198 |
| 4,681,567 | 7/1987 | Maskess et al. | 604/198 |
| 4,702,738 | 10/1987 | Spencer | 604/198 |
| 4,737,144 | 4/1988 | Choski | 604/198 |
| 4,738,633 | 4/1988 | Bogan | 604/198 |

*Primary Examiner*—John D. Yasko
*Attorney, Agent, or Firm*—Polster, Polster and Lucchesi

[57] ABSTRACT

A protective sleeve for the needle of a hypodermic syringe includes a formed resilient plastic body. The body is split longitudinally to form slightly greater than a semicylinder. The body is snapped onto the barrel of a hypodermic needle before or after the needle is used. It may be slid longitudinally over the needle to protect against accidental puncture by the needle after the needle is used and locks into this position.

16 Claims, 1 Drawing Sheet

U.S. Patent
Aug. 7, 1990
4,946,447
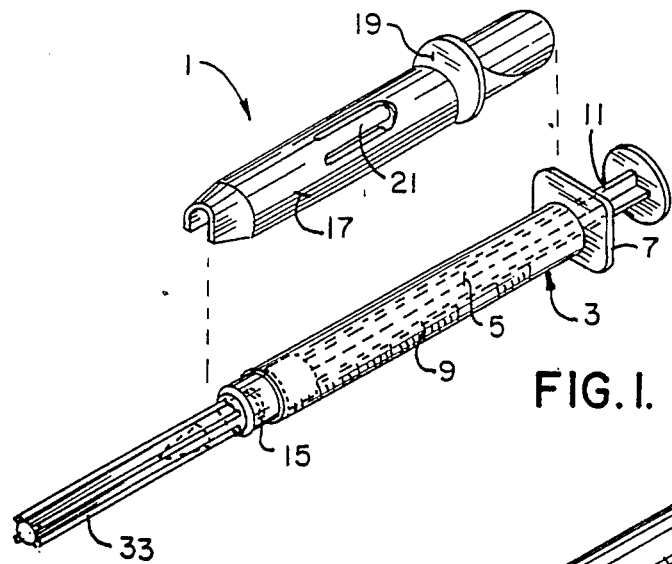
FIG.1.
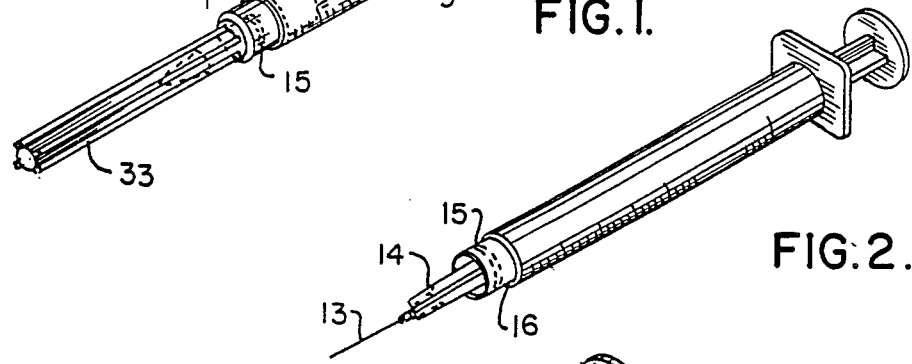
FIG.2.
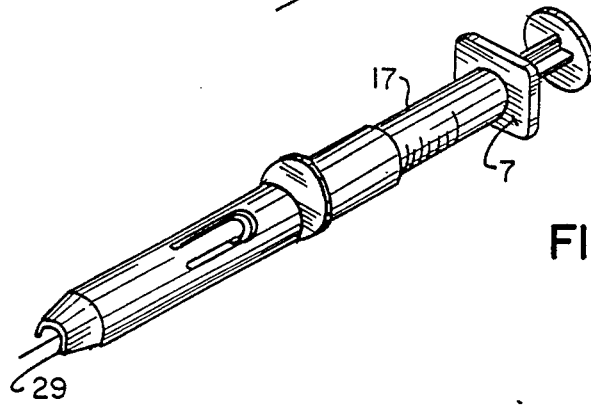
FIG.3.
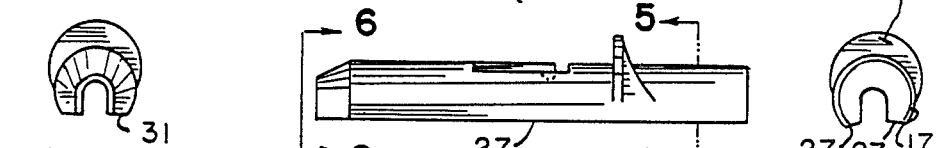
FIG.6. FIG.4. FIG.5.
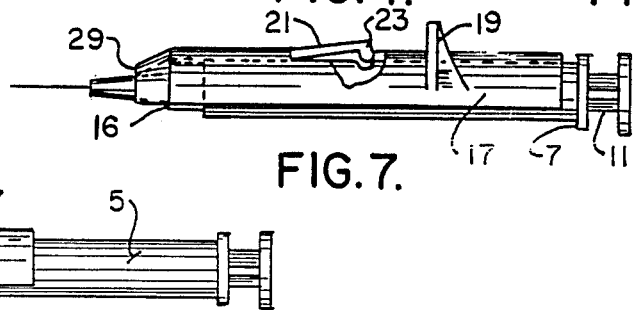
FIG.7.
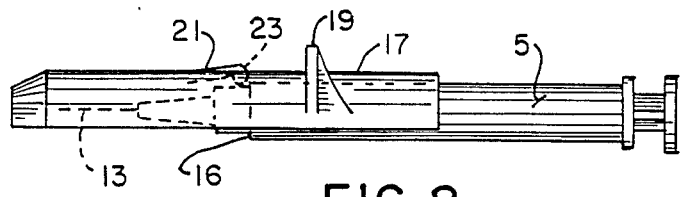
FIG.8.

PROTECTIVE COVER FOR HYPODERMIC NEEDLE

Background of the Invention

This invention relates to safety shields for hypodermic syringes and in particular to an inexpensive shield for covering the point of the needle of a disposable hypodermic syringe after it has been used.

Hypodermic syringes are used to administer medicaments under the skin and into the patient's body (i.e. subcutaneously, intravenously, intramuscularly, etc.). Because patients potentially carry infectious diseases, the needle of a used syringe will potentially be contaminated with an infectious disease. Anyone accidentally stuck by a contaminated needle may contract the disease. It is thus important to protect the user who must recap the needle, all those in the immediate vicinity who could accidentally come into contact with the needle, and cleaners and trash collectors who could be stuck by loose or inadequately covered needles in the trash. To provide this protection, a protective cover is needed which is easily operable, which can be quickly put into place on the syringe covering the needle and which will stay in place. The need is especially acute for home users, such as diabetics using insulin, who generally have no formal means of disposing of used syringes.

Prior art is replete with attempts to design a satisfactory safety shield. Many have two or more pieces and are complicated to attach to the syringe and are complicated to use. Most require specially designed syringes, to which the shield is attached before shipment to the consumer. Many obstruct the syringe's measuring marks, making it difficult to fill the syringe accurately.

Summary of the Invention

One of the objects of the present invention is to provide a simple one-piece protective shield for hypodermic syringes.

Another object is to provide such a shield which can quickly, easily, and effectively attach to most manufacturers' standard syringes either before or after the syringe has been filled or used.

Another object is to provide such a protective shield which will not obstruct the measuring marks on the body of the syringe.

Yet another object is to provide a protective shield which may be produced and shipped inexpensively.

These and other objects will become more apparent to those skilled in the art upon a review of the following description in light of the accompanying drawings.

In accordance with the present invention, generally stated, a protective cover for a hypodermic needle is provided wherein the protective covering comprises an elongate resilient sleeve which includes a longitudinal slit or aperture extending its entire length. The sleeve is sized and proportioned to be snapped laterally onto the hypodermic syringe. Once snapped into a retracted position on the syringe, the sleeve is axially slidable on the syringe to an extended position in which it covers the needle of the syringe. Tab means are provided on the sleeve to keep the sleeve from retracting from its extended position. The tab is integrally molded into the sleeve.

The sleeve is preferably cylindrical, subtending an angle of from slightly greater than 180° to an angle of 270° or more in cross-section. The size of the longitudinal aperture is chosen to permit the sleeve to be snapped easily and securely onto the syringe, and is therefore dependent on the material of which the sleeve is made. The diameter of the sleeve and its material are preferably chosen to grip the syringe body snugly. Therefore, the sleeve may be moved manually to its extended position without undue effort, but it frictionally resists further forward movement off the syringe body when it is in its extended position. The sleeve is preferably made of a plastic material which is sufficiently resilient to permit the sleeve to be snapped onto the syringe body.

The sleeve preferably is tapered at its forward end to provide a smaller diameter section around the tip of the needle. The tapered portion also includes a longitudinal aperture which is continuous with the longitudinal aperture in the major portion of the sleeve body. The size of the longitudinal aperture in the tapered portion may differ from that in the rest of the sleeve body, because it must clear an adapter portion of the syringe which is much smaller in diameter than the body of the syringe.

The tab means preferably includes a resilient finger integrally molded into the sleeve. The finger has, at its distal end, a protrusion projecting radially inwardly into engagement with the syringe body and engaging an axial end of the syringe body when the sleeve is in its extended position.

The sleeve also preferably includes a protruding integral thumb rest for pushing the sleeve to its extended position. The thumb rest is proportioned and positioned to permit the user to extend the sleeve to its protective position by a single movement of straightening the thumb while grasping the syringe with one hand.

In use, the protective sleeve is snapped on from the side. Because the sleeve is formed of a clear plastic material, and because its axial aperture may extend circumferentially from about 60° to almost 180°, the sleeve does not obscure measurement markings on the syringe. It therefore may be snapped onto the syringe before it is filled. Because the sleeve is snapped on from the side, rather than slid axially onto the syringe, it may also be placed on the syringe after it is filled or even after it is used, without substantial risk of pricking the user.

The user moves the sleeve to its extended position by grasping a flange on the syringe with the fingers of one hand and pushing the thumb rest with his thumb down the body of the syringe until the tab passes the end of the syringe body and the tab snaps down. The sleeve is then prevented from retracting because the tab is blocked by the body of the syringe.

Although the sleeve does not completely surround the needle in its extended position, it has been found to provide remarkably complete protection against contact of even a small finger with the needle. For a relatively small (three milliliter) syringe, the sleeve provides adequate protection even without the tapered section.

Brief Description of the Drawings

FIG. 1 is an exploded view in perspective of a protective shield of the present invention and a hypodermic syringe on which it is to be positioned.

FIG. 2 is a perspective view of the hypodermic syringe of FIG. 1, with a protective cap removed from the needle of the syringe.

FIG. 3 is a perspective view of the protective shield and syringe of FIGS. 1 and 2, with the shield in a partially extended position.

FIG. 4 is a view in side elevation of the shield of FIGS. 1 and 3.

FIG. 5 is a sectional view taken along the line 5—5 of FIG. 4.

FIG. 6 is a sectional view taken along the line 6—6 of FIG. 4.

FIG. 7 is a view in side elevation of the shield of FIGS. 1 and 3–6, showing the shield in a retracted position on the syringe of FIGS. 1–3.

FIG. 8 is a view in side elevation, corresponding to FIG. 7, showing the shield in an extended position.

Description of the Preferred Embodiment

Referring now to the drawings, reference numeral 1 indicates a protective shield in the form of a sleeve which is snappably attachable to a syringe 3 and slidable thereon.

The syringe 3 is of the type which includes a cylindrical hollow body 5 having a flange 7 integral with the rear thereof and measuring marks 9 inscribed thereon. A plunger 11 fits inside the rear of the body 5 and is axially slidable therein. An elongate hollow needle 13 communicates with the interior of the body 5. A fitting 14 carries the needle, for attaching the needle to the body 5. A nose 15 integrally formed on the forward end of the body receives the needle fitting 14. The nose 15 is of smaller diameter than the body 5, so that an axial wall 16 is formed at the forward end of the body 5. Syringes of this general type are widely available from a number of manufacturers. The diameters of syringes of particular sizes are also generally standardized. For example, the diameter of the body 5 of a three-milliliter syringe is generally about one centimeter.

The sleeve 1 is molded of transparent polystyrene having a nominal wall thickness of about one millimeter. The sleeve 1 comprises a main body section 17, having a protruding thumb rest 19 and a finger 21 which has an inwardly protruding tab 23 at its free rearward end, and a frusto-conical forward section 25.

The main body section 17 has an inner diameter of one centimeter, to conform to the body 5 of the syringe 3, and a length of seven centimeters. The length of the body section 17 is determined by the length of the body 5 and needle 13 of the syringe, and may vary from about five centimeters to about eight centimeters. The body section 17 is generally circularly cylindrical in shape, and includes a longitudinal aperture defined by longitudinal edges 27 extending the length of the main body section 17. The body section 17 subtends an angle of about 240°. The longitudinal edges 27 of the main body section 17 are therefore spaced apart about 0.87 centimeters, and must spread about 0.13 centimeters to snap over the syringe 3.

The thumb rest 19 is spaced about two centimeters from the rear axial end of the sleeve, to provide sufficient room for the user's thumb even when the sleeve is positioned against the flange 7 of the syringe.

The finger 21 is defined by a thin U-shaped opening in the wall of the main body section 17. The finger 21 is about 1.5 centimeters long and about 1.5 millimeters wide. In its relaxed position, the finger 21 lies substantially in the same plane as the wall of the main body section 17. At the distal end of the finger, tab 23 extends inwardly (toward the syringe when the sleeve is mounted on it) about one to two millimeters.

Both the thumb rest 19 and the finger 21 are centered circumferentially on the main body section 17.

The tapered section 25 is about 0.5 centimeters long, and forms a frusto-conical segment having an inner diameter, at its forward end 29, of about 5 millimeters. The edges 31 of the tapered section 25 form smooth continuations of the edges 27 of the body section 17, so that a continuous slit or longitudinal aperture is formed from one end of the sleeve 3 to the other. The space between the edges 31 decreases toward the forward end of the sleeve 1, to about 0.50 centimeters, the diameter of the front opening 29. The tapered section serves to prevent the sleeve from being put onto the syringe backwards, and also reduces the size of the opening in the neighborhood of the tip of the needle when the sleeve is moved to its extended position.

The sleeve may easily be snapped onto the syringe 3 from the side without breaking When the sleeve 1 is snapped onto the syringe in its retracted position, the main body part 17 of the sleeve extends from the nose 15 of the syringe up the syringe nearly to its flange 7. The tapered section 25 of the sleeve covers the nose 15 of the syringe and a part of the needle attachment means 14, but it does not extend out over the needle 13. The finger part 21 is flexed away from the syringe body by the tab 23.

Because the sleeve is snapped on laterally from the side, rather than being slid longitudinally over the syringe, the dangers of a slide-on sleeve are not present and the sleeve may be snapped on before or after injection. Further, because the edges 27 define a fairly wide slot, the measuring marks 9 are unobstructed and the sleeve 1 may be snapped on prior to filling the syringe with medicament without any risk of optical distortion by the sleeve.

As shown in FIG. 1, hypodermic syringes are packaged with a protective cap 33 over the needle. In the preferred embodiment of sleeve 3, the front opening 29 of the sleeve may be too small to accommodate the cap 33. For syringes with such large caps, the cap must be removed before the sleeve is installed.

After the needle has been used and is ready to be covered, the user simply moves his thumb from the plunger 11 to the thumb rest 19, without removing his grip on the syringe flange 7, and pushes on the flange 19. As the user's thumb straightens, it slides the sleeve down the syringe and into its extended position covering the needle 13. The sleeve is slid down until the tab 23 at the end of the finger 21 snaps down audibly as it passes over the nose 15 of the syringe 3. When the finger 21 snaps down, the needle will be fully covered, with the end 29 of the sleeve 3 several millimeters beyond the end of the needle 13. The distance moved by the sleeve 3 before the tab 23 engages the end 16 of the syringe body also corresponds generally to the distance moved by straightening the thumb, so that the sleeve may be moved to its extended, protective, position in a single motion. The tab 23 engages the axial wall 16 of the syringe body 5 and prevents the sleeve from retracting.

It has been found that the sleeve 3 provides excellent protection against accidental pricking by the needle, despite the relatively wide slit 31 extending adjacent the end of the needle.

Numerous variations, within the scope of the appended claims, will be apparent to those skilled in the art in light of the foregoing description and accompanying drawings. Merely by way of example, a single diameter slidable sleeve may be used. It has been found that a one centimeter sleeve extending only a few millimeters beyond the end of the needle provides excellent protection even when the sleeve subtends an angle substantially less than 270 degrees. Parts of the sleeve may be omitted, with the attendant loss of their function. The shape of the sleeve could be other than circularly cylindrical. The tapered forward part of the sleeve could be somewhat offset from the axis of the main body section. The longitudinal edges of the sleeve could be turned to facilitate snapping the sleeve onto the syringe. The syringe may be shipped in a sterile bag with the sleeve 3 in its extended position, with or without a protective cap 33. A separate cap, possibly hinged to the forward end of the sleeve 3, may be provided for closing the sleeve, when it is in its extended position. Lifting the finger 21 permits the sleeve 3 to be slid back to its retracted position. An additional stop may be provided for preventing the sleeve from being pushed forward off the end of the syringe. For example, a clip may be provided for attachment to the flange 7 of the syringe 3, and the clip may be attached to the rearward end of the sleeve 1 by a flexible or hinged strap; the clip and strap may be integrally molded with the sleeve. The sleeve may be made of other resilient materials, such as impact-modified acrylic or nylon. These variations are merely illustrative.

We claim:

1. In the combination of a hypodermic syringe assembly having a cylindrical body for holding a medicament, a hollow needle at a forward end of said body for administering said medicament, and an axially slidable plunger to force said medicament out of said body through said needle, and a protective cover slidable on said body from a retracted position exposing said needle to an extended position extending axially beyond said needle, the improvement wherein said protective cover comprises a resilient semicylindrical sleeve having a longitudinal slit extending its entire length, said sleeve being sized and constructed to be placed laterally onto said hypodermic syringe through said slit, and tab means for locking said sleeve in its extended position.

2. The improvement of claim 1 wherein said sleeve subtends an angle between 180° and 300°.

3. The improvement of claim 1, wherein said tab means comprise a resilient finger integral with the sleeve.

4. The improvement of claim 3 wherein the finger is generally coplanar with the surrounding portion of the sleeve and includes a tab part at a distal end of the finger, the tab part extending toward said body.

5. The improvement of claim 4 wherein said tab abuts an axial end of said syringe body when said sleeve is in said extended position.

6. The improvement of claim 1 wherein said sleeve further comprises a raised thumb rest spaced from a rearward end of said sleeve, for engagement by a thumb of a user to move said sleeve from said retracted position to said extended position.

7. The improvement of claim 6 wherein said sleeve includes a main body part sized to grasp said syringe body frictionally, and a tapered forward part for covering said needle when said sleeve is in its forward position.

8. The improvement of claim 1 wherein said sleeve includes a main body part sized to grasp said syringe body frictionally, and a tapered forward part for covering said needle when said sleeve is in its forward position.

9. In the combination of a hypodermic syringe assembly having a cylindrical body for holding a medicament, a hollow needle at a forward end of said body for administering said medicament, and an axially slidable plunger to force said medicament out of said body through said needle, and a protective cover slidable on said body from a retracted position exposing said needle to an extended position extending axially beyond said needle, the improvement wherein said protective cover comprises a resilient semicylindrical sleeve having a longitudinal slit extending its entire length, said sleeve being sized and constructed to be placed laterally onto said hypodermic syringe through said slit, said sleeve further comprising a raised thumb rest spaced from a rearward end of said sleeve, for engagement by a thumb of a user to move said sleeve from said retracted position to said extended position.

10. The improvement of claim 9 wherein said sleeve subtends an angle between 180° and 300°.

11. The improvement of claim 9 wherein said sleeve includes a main body part sized to grasp said syringe body frictionally, and a tapered forward part for covering said needle when said sleeve is in its forward position.

12. In the combination of a hypodermic syringe assembly having a cylindrical body for holding a medicament, a hollow needle at a forward end of said body for administering said medicament, and an axially slidable plunger to force said medicament out of said body through said needle, and a protective cover slidable on said body from a retracted position exposing said needle to an extended position extending axially beyond said needle, the improvement wherein said protective cover comprises a resilient semicylindrical sleeve having a longitudinal slit extending its entire length, said sleeve being sized and constructed to be placed laterally onto said hypodermic syringe through said slit, said sleeve including a main body part sized to grasp said syringe body frictionally, and a tapered forward part for covering said needle when said sleeve is in its forward position.

13. The improvement of claim 12 wherein said sleeve subtends an angle between 180° and 300°.

14. A method for covering a hypodermic syringe having a body and a needle extending therefrom, said method comprising a step of snapping onto said syringe from the side a slidable sleeve having a longitudinal slot extending the length of said sleeve, and a step of sliding said sleeve down said body of said syringes until said needle is covered, said slidable sleeve comprising a finger having a free end, said step of sliding said sleeve comprising sliding said sleeve until said finger snaps down over a forward end of said syringe body.

15. The method of claim 14 wherein the syringe body includes a flange at an end opposite the needle, and wherein the sleeve includes a protruding thumb rest, the step of sliding said sleeve to an extended position comprising grasping the syringe including the flange with one hand, and placing the thumb of said hand on the thumb rest to slide the sleeve forward.

16. A method for covering a hypodermic syringe having a body and a needle extending therefrom, said method comprising a step of snapping onto said syringe from the side a slidable sleeve having a longitudinal slot extending the length of said sleeve, and a step of sliding said sleeve down said body of said syringes until said needle is covered, the syringe body including a flange at an end opposite the needle and the sleeve including a protruding thumb rest, the step of sliding said sleeve to an extended position comprising grasping the syringe including the flange with one hand, and placing the thumb of said hand on the thumb rest to slide the sleeve forward.

* * * * *